United States Patent [19]

Carpenter et al.

[11] Patent Number: 4,897,353

[45] Date of Patent: Jan. 30, 1990

[54] CRYOGENIC PROTECTION OF PHOSPHOFRUCTOKINASE USING AMINO ACIDS AND ZINC IONS

[75] Inventors: John F. Carpenter, David, Calif.; Steven C. Hand, Louisville, Colo.; Lois M. Crowe; John H. Crowe, both of Davis, Calif.

[73] Assignee: University of Southwestern Louisiana, Lafayette, La.

[21] Appl. No.: 924,794

[22] Filed: Oct. 30, 1986

Related U.S. Application Data

[63] Continuation-in-part of Ser. No. 839,330, Mar. 13, 1986, Pat. No. 4,806,343.

[51] Int. Cl.[4] ............................ C12N 9/96; C12N 9/12
[52] U.S. Cl. .................................... 435/188; 435/194; 435/814
[58] Field of Search ........................ 435/188, 814, 194; 530/303, 304, 402, 344, 412; 564/297

[56] References Cited

U.S. PATENT DOCUMENTS 3,124,517  3/1964  Eloy ........................................ 195/66
4,169,012  9/1979  Dawson et al. ........................ 435/7

OTHER PUBLICATIONS

Carpenter, J. F. et al. (1986), Arch. Biochem. Biophys. 250(2), 505–512.
Hand, S. C. et al. (1982), J. Biol. Chem., 257(2), 734–741.
Heber, U. et al. (1971), Biochim. Biophys. Acta 241, 578–592.

Primary Examiner—Thomas G. Wiseman
Assistant Examiner—Charles L. Patterson, Jr.
Attorney, Agent, or Firm—Keaty & Keaty

[57] ABSTRACT

A method of protecting soluble proteins such that their biological activity is preserved after freezing by exposing the protein to an amino acid or trimethylamine-N-oxide and transition metal ion prior to freezing. The protected protein can then be thawed without denaturation or impairment of the protein's biological activity. The protein is preferably exposed to the amino acid or trimethylamine-N-oxide by placing it in a 25–100 mM aqueous solution of organic solute and 1 mM $Zn^{+2}$. This method is especially effective in preserving the biological activity of fragile proteins such as the enzyme phosphofructokinase. The present method can be used to preserve pharmaceutically useful proteins in a frozen form for storage and distribution. The treated protein can be thawed and administered directly to a user without removing the cryoprotectant since the amino acid or oxide and trace amounts of many transition metal ions are nontoxic.

4 Claims, 1 Drawing Sheet

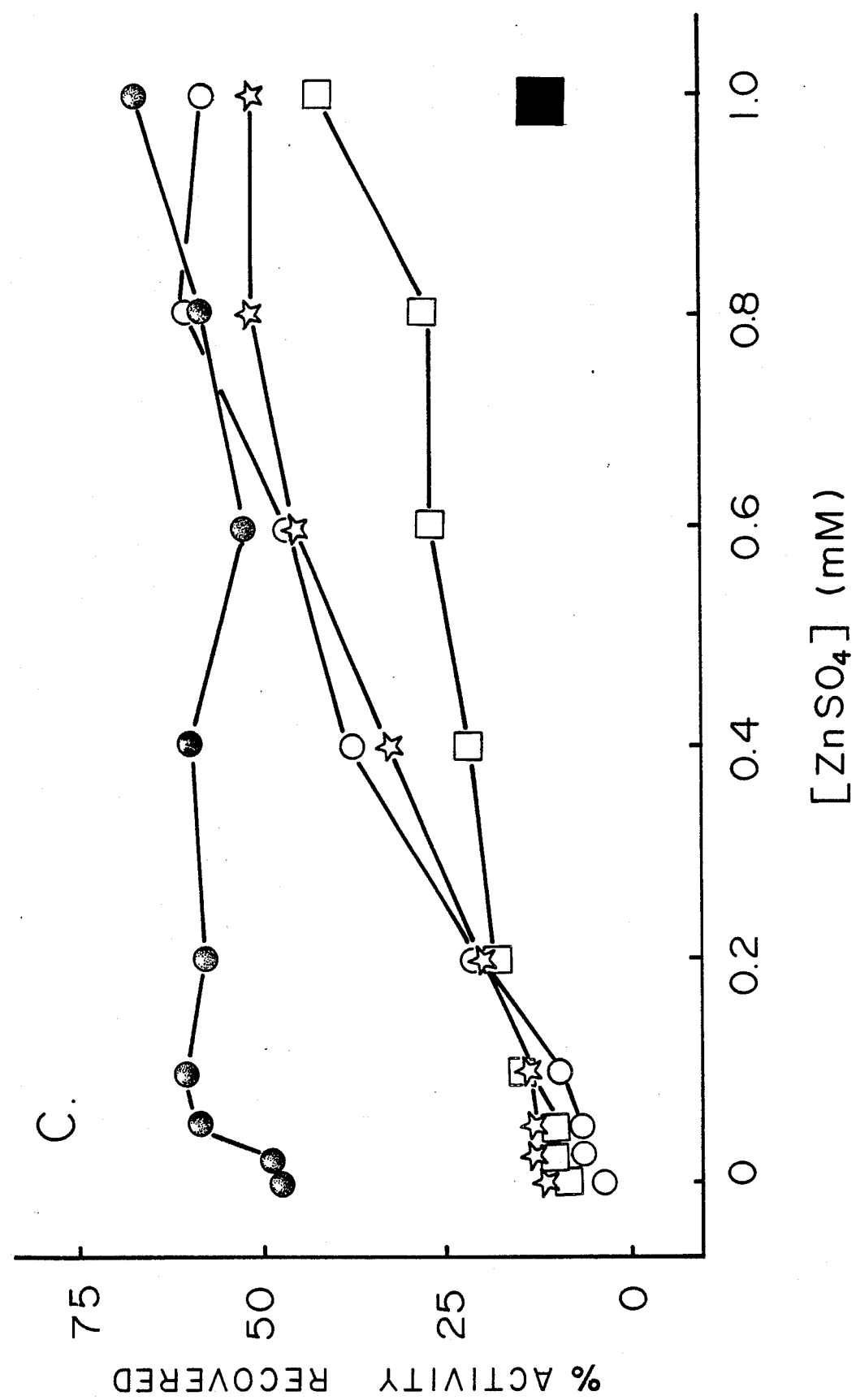

CRYOGENIC PROTECTION OF PHOSPHOFRUCTOKINASE USING AMINO ACIDS AND ZINC IONS

CROSS REFERENCE TO RELATED APPLICATION

This is a continuation-in-part of U.S. patent application Ser. No. 839,330, filed Mar. 13, 1986, now U.S. Pat. No. 4,806,343, Feb. 21, 1989, the disclosure of which is incorporated by reference.

BACKGROUND OF THE INVENTION

1. Field of the Invention

This invention concerns a method of protecting proteins such that their biological activity is preserved after freezing. This protection is achieved by adding a cryoprotectant that preserves biological activity of the protein in spite of freezing. More particularly, the invention concerns a method for preserving therapeutically effective proteins so that they can be conveniently stored in a nonliquid form while retaining substantially all of their biological acitivity.

2. General Discussion of the Background

Proteins are one of the almost universal constituents of living organisms. The fragility of living organisms and their usual ability to survive only within very narrow ranges of environmental conditions can be explained by a protein's loss of biological activity outside of a relatively narrow temperature range. For example, freezing often permanently changes the three dimensional tertiary structure of proteins, usually resulting in a loss of biological activity.

An especially sensitive kind of protein is an enzyme. Enzymes are polypeptide molecules that are produced by living cells and catalyze specific biochemical reactions at body temperatures. An example of such an enzyme is phosphofructokinase (PFK) which is a rate limiting catalyst in the glycolytic pathway. PFK catalyzes the addition of a phosphate group to fructose 6-phosphate, but once the enzyme is frozen it irreversibly loses all catalytic activity.

Since proteins play an important role in the function and regulation of living organisms, proteins have also become useful pharmaceutical agents. For example, the pancreatic protein insulin is instrumental in controlling animal blood sugar levels. If an animal's production of insulin is impaired, the resulting physiological condition is known as diabetes. This disease is usually treated by injecting specific doses of insulin into the animal. The cost and inconvenience of such treatment is increased, however, by the necessity of refrigerating the insulin in liquid form to preserve its biological activity until it is administered to a patient. Even at refrigeration temperatures, however, the protein is unstable and loses some of its activity. It would therefore be desirable to freeze such proteins to give them a longer shelf life.

It is not presently possible to simply freeze a protein such as insulin because freezing and subsequent thawing, or lyophilization and subsequent rehydration, usually diminishes the biological activity of the protein. This problem has resulted in efforts to find ways to preserve the biological activity of proteins after they are frozen.

For example, U.S. Pat. No. 4,180,917 discloses a multistep process for freeze-drying enzymes in which the enzymes typically recover about 75 to 85% of their biological activity following freeze-drying. The method is complicated by the need for concentrating the enzyme solution using reverse osmosis or ultrafiltration and adding water insoluble salts. The protease and alpha-amylase compositions treated by this method are also quite stable to begin with and would retain a substantial amount of their activity after freezing even without addition of insoluble salts and reverse osmosis.

U.S. Pat. No. 3,607,858 describes a method of freeze-drying human blood proteins in the presence of small amounts of nonionic surface active agents with very rapid freezing in small containers. The globulins treated by this method are already quite stable to freezing and would survive freeze-drying even without addition of surface active agent. The addition of the nonionic surfactant simply serves to speed up the process of redissolving the globulin.

Although not dealing with preservation of proteins, U.S. Pat. No. 4,134,214 discloses that a polysaccharide antigen can be preserved by freeze-drying it at temperatures of $-20°$ to $-40°$ C.

Similarly unrelated to protein preservation is the work of Crowe et al. at the University of California-Davis with liposomes. A liposome is an artificial vesicle comprised of one or more concentric phospholipid bilayers. Crowe has shown, for example, in *Science*, Vol. 223, pp. 701–703 (Feb. 17, 1984), that addition of trehalose alone to liposomes allows them to be freeze-dried and rehydrated without disruption of their phospholipid membranes. The mechanism of protection suggested by Crowe is a direct interaction between the phospholipid polar head groups and trehalose that prevents adhesion between the head groups during freezing. Crowe also believes that trehalose reduces the transition temperature of the liposomes and inhibits thermotropic gel to liquid crystalline phase transitions that are known to result in leakage of the contents of hydrated phospholipid vesicles.

The prior art had suggested that cryoprotectants such as dimethylsulfoxide (DMSO) and glycerol extend protective action on proteins by altering the structure of the water solvent through a thermodynamic effect. Gekko et al., *Biochemistry* 20:4667–4676 (1981). It would therefore not be predicted that substances such as trehalose would protect since Crowe had taught that the mechanism of trehalose action was one of direct interaction with the substance being protected.

The use of prior cryoprotectants, such as DMSO, with proteins present serious problems since DMSO and other cryoprotectants are biologically incompatible materials. If such an incompatible material were added to proteins, the cryoprotectant had to be removed prior to use of the protein in a biological system to prevent toxic reactions. If the incompatible material had reducing properties, it could also cause "protein browning" which diminishes or destroys the activity of the protein and turns it brown. This protein browning phenomenon is discussed in Lea, C. H. and R. S. Hanna, *Biochim. Biophys. Acta.*, 3:313 (1949), Lea, C. H. and R. S. Hannan, *Biochim. Biophys. Acta.*, 4:518 (1950); Lea, C. H. and R. S. Hannan, *Biochim. Biophys. Acta.*, 5:433 (1950); Lea, C. H. and R. S. Hannan, *Nature*, 165:438 (1950); Feeney, R. E., G. Blankenhorn and H. Dixon, Adv. Prot. Chem., 29:135 (1975).

Another problem with prior art cryoprotectants such as DMSO and glycerol is that they must be present in solution in several molar amounts before they exert their cryoprotective influence. Such excessive amounts of an additive can disrupt biological function and are difficult to remove.

It is accordingly an object of this invention to provide a method of protecting proteins such that their biological activity is preserved after freezing.

Another object of the invention is to provide such a method of preservation which will protect the protein during freezing and thawing.

Yet another object of the invention is to provide such a method of preservation which employs only nontoxic, biologically compatible additives.

Still another object of the invention is to provide such a method that will permit proteins, such as therapeutically useful substances and enzymes, to be frozen and thawed or lyophilized and rehydrated while retaining the majority of their biological activity.

Even yet another object is to provide a cryogenic protectant additive for proteins which is nonreducing and does not cause protein browning.

Finally, it is an object to provide such a method which employs only a very low concentration of a cryoprotectant additive which is nontoxic and can be administered to an animal along with a therapeutic protein.

SUMMARY OF THE INVENTION

The aforementioned objects are achieved by providing a method of protecting proteins such that their biological activity is preserved after freezing by exposing the protein to trimethylamine-N-oxide or an amino acid and a transition metal ion, and then freezing the protein. In preferred embodiments, the protein is exposed to 1 mM $Zn^{+2}$ and a 50 to 100 mM concentration of an amino acid in an aqueous solution. By adding as little as a 50 mM concentration of amino acid with 1 mM $Zn^{+2}$ to the solution, the protein will retain much of its biological activity.

In an alternate embodiment, cryoprotection is achieved by exposing the protein to trimethylamine-N-oxide (($CH_3)_3NO$) alone or in combination with a transition metal ion, such as $Zn^{+2}$. The trimethylamine-N-oxide alone exhibits significant cryoprotection properties which are further enhanced by addition of the transition metal ion.

In other embodiments, the protein could be dialyzed to remove the cryoprotectant additives, if desired. Amino acids and transition metal ion are not very effective as cryoprotectants in freeze drying.

In other embodiments, the protein and cryoprotectant are frozen and stored without loss of the proteins' biological activity. Freezing the protein greatly extends it shelf life as compared to the shelf life of proteins which are simply refrigerated.

Divalent transition metal ions such as $Zn^{+2}$, $Cu^{+2}$, $Cd^{+2}$, $Ni^{+2}$, and $Co^{+2}$, in combination with an amino acid, protect proteins from loss of biological activity due to freezing. This cryoprotective property is observed with even trace amounts of $Zn^{+2}$, for example, about 0.2 mM $ZnSO_4$ solution. The preferred concetrations of the transition metal ion are greater than 0.4 mM and more preferably about 1 mM or more.

In the presence of transition metal ion, cryoprotection is observed with amino acids such as proline, 4-hydroxyproline, and glycine.

Trimethylamine-N-oxide provides significant cryoprotection at 50 mM concentrations. Addition of trace amounts of transition metal ion, for example about 0.1 mM $Zn^{+2}$, increases cryoprotection.

BRIEF DESCRIPTION OF THE DRAWING

The drawing is a graph of percentage biological activity recovered by phosphofructokinase after freezing and thawing in the presence of varying concentrations of $ZnSO_4$ in a 50 mM aqueous solution of each of the following: trimethylamine-N-oxide, proline, 4-hydroxyproline, glycine, and no organic solute.

DETAILED DESCRIPTION

The term "soluble proteins" refers to proteins that are not bound in membranous structures such as cell membranes. The following data is limited to studies of soluble proteins since it is difficult to assess retention of biological activity of membrane-bound proteins. The presence of other biological struttures in the cell membrane might affect findings of biological activity retained, hence the following data concern solely soluble proteins. The present invention is not limited, however, to cryoprotection of soluble proteins alone.

The enzyme phosphofructokinase (PFK) is used as one of the model proteins for the following cryoprotective studies. It was chosen for study since it is known to be ultrasensitive to cold and freezing, usually losing all biological activity after being frozen. Most other enzymes are also quite sensitive to loss of substantial biological activity after freezing and upon thawing.

The term "transition metal" is herein defined to include the elements appearing in Groups IB through VIIIB of the Periodic Table of the Elements.

Previous copending U.S. patent application Ser. No. 839,330, filed Mar. 13, 1986, now U.S. Pat. No. 4,806,343, describes cryoprotection of proteins by exposing the proteins to a carbohydrate and transition metal ion. In a preferred embodiment, the carbohydrate was trehalose and the metal ion was $Zn^{+2}$. The present application concerns cryoprotection of proteins by exposing them to amino acids and a transition metal ion, trimethylamine-N-oxide, or trimethylamine-N-oxide and a transition metal ion.

EXAMPLE I

To avoid complications due to enzyme absorption to glass, all phases of the freeze-thaw experiments were performed in polypropylene Eppendorf test tubes. To prepare the PFK enzyme for freezing, PFK was dialyzed overnight against a 1 mM sodium borate buffer (pH 7.8 at 23° C.) containing 5 mM dithiothreitol, 2 mM $(NH_4)_2 SO_4$ and 25 mM $K_2SO_4$. Then 10 microliters of the enzyme stock were added to 115 microliters of 1 mM $ZnSO_4$ and the amino acid glycine in aqueous solution (prepared in the above buffer) in polypropylene Eppendorf centrifuge tubes to give a final PFK concentration of approximately 0.025 mg/ml and a desired glycine concentration of 50 mM. Duplicate assays of this enzyme-cryoprotectant solution were made for PFK catalytic activity following the fructose 1,6-biphosphate-coupled procedure of Bock and Frieden, *J. Biol. Chem.*, 251:5630–5636 (1976). In this procedure, a Perkin-Elmer dual beam spectrophotometer Model 550 was used to measure disappearance of NADH, which absorbs at 340 nm. Then 75 microliters of the enzyme-cryoprotectant solution were transferred to another Eppendorf centrifuge tube and frozen by immersion in liquid nitrogen for 30 seconds. The enzyme preparation was then thawed at room temperature and assayed immediately in the spectrophotometer for catalytic activity at 25° C. The values of percentage activity recovered were expressed as a percentage of the activity measured prior to freezing. A residual control sample (never frozen) was checked again for catalytic activity to ensure that it was stable during the experimental time period.

Using this procedure, PFK was found to recover about 60% of its catalytic properties when treated in a 1 mM $ZnSO_4$ and 50 mM aqueous solution of glycine prior to freezing.

EXAMPLE II

The procedure of Example I was repeated using the following concentrations of $ZnSO_4$ in the presence of 50 mM glycine: 0.1 mM, 0.2 mM, 0.4 mM, 0.6 mM, and 0.8 mM. The percentage of enzymatic activity recovered at each of these concentrations is shown in the drawing.

EXAMPLE III

The procedure of Example I would be repeated using 50 mM glycine and a 1 mM concentration of the following salts instead of $ZnSO_4$: $MnSO_4$, $CuSO_4$, $NiCl_2$, $CoCl_2$, and $CdCl_2$. These are all salts of transition metals which will dissociate in solution to provide transition metal ions.

EXAMPLE IV

The enzyme PFK was prepared and frozen with glycine as described in Example I, except no cation was added. After freezing, the PFK showed only minimal enzymatic activity. This data is also included in the drawing at the point on the graph where $ZnSO_4$ is zero.

EXAMPLE V

The enzyme PFK was prepared and frozen in the presence of 1 mM $ZnSO_4$ as described in Example I, except the enzyme was separately treated with a 50 mM concentration of the amino acid proline and then the amino acid 4-hydroxyproline at the following concentrations of $ZnSO_4$: 0, 0.2, 0.4, 0.6, 0.8, and 1.0.

The percentage of biological activity recovered in each instance is shown in the drawing. For comparison, the percentage enzymatic activity retained by PFK following freezing and thawing in the presence of the amino acid with no $ZnSO_4$ is also shown in the drawing. The combination of amino acid and $Zn^{+2}$ provides cryoprotection for the PFK, the amount of cryoprotection (as measured by percent activity recovered) increasing with increasing concentration of $Zn^{+2}$.

EXAMPLE VI

The procedure of Example I using 1 mM $Zn^{+2}$ was repeated except 50 mM trimethylamine-N-oxide was substituted for the amino acid glycine. About 70% of biological activity was recovered, as shown in the drawing.

The procedure was repeated using the 50 mM trimethylamine-N-oxide in place of the amino acid except the concentration of $ZnSO_4$ was varied as follows: 0, 0.2, 0.4, 0.6, and 0.8 mM. Percentage of biological activity retained remained fairly constant across this range of $Zn^{+2}$ concentrations. Even when $Zn^{+2}$ was eliminated altogether (0 mM $ZnSO_4$), PFK recovered about 48% of its biological activity. It therefore appears that trimethylamine-N-oxide acts as a cryoprotectant for proteins even without the presence of a transition metal ion.

EXAMPLE VII

Human insulin for treatment of diabetes is usually packaged in dosage units, with about 40 units per milligram of insulin. A 100 unit vial of human insulin such as that sold by Eli Lilly and Co. under the trademark HUMULIN would be prepared and exposed to 50 mM glycine and 1 mM $Zn^{+2}$ as described in Example I. The insulin would then be frozen and stored in a freezer until ready for use, thereby prolonging the shelf life of the drug. A user would remove the insulin from the freezer and thaw it prior to use. The thawed insulin and glycine/$Zn^{+2}$ would be injected into a user without removing the glycine and $Zn^{+2}$ would be injected into a user without removing the glycine and $Zn^{+2}$ from solution.

EXAMPLE VIII

The procedure of Example VII would be repeated, except the glycine and $Zn^{+2}$ would be removed by dialysis from the insulin after thawing or rehydration and prior to injection.

EXAMPLE IX

The procedure of Example VIII would be repeated using therapeutically useful proteins and peptides other than insulin. Examples of such pharmaceutical proteins include interferon, beta-endorphin, lymphokines, interleukins, peptide growth factors, and numerous peptide hormones. Example of the peptide hormones that could be preserved by this method include vasopressin, transferrin, relaxin, prolactin, and growth hormone.

Having illustrated and described the principles of the invention in a preferred embodiment, it should be apparent to those skilled in the art that the invention can be modified without departing from such principles. I claim all modifications coming within the spirit and scope of the following claims.

We claim:

1. A method of protecting phosphofructokinase against loss of biological activity due to freezing, the method comprising:
   prior to freezing, exposing phosphofructokinase (PFK) to effective stabilizing amounts of $Zn^{+2}$ and an amino acid selected from the group consisting of proline, 4-hydroxyproline and glycine.

2. The method of claim 1 wherein said step of exposing said PFK to said amino acid comprises placing said PFK in a solution comprised of about a 50 mM concentration of amino acid.

3. The method of claim 1 wherein the concentration of $Zn^{+2}$ is at least about 1 mM.

4. A composition consisting essentially of phosphofructokinase (PFK), $Zn^{+2}$ and an amino acid selected from the group consisting of proline, 4-hydroxyproline and glycine, said $Zn^{+2}$ and amino acid being present in an amount effective to stabilize said PFK against loss of biological activity due to freezing.

* * * * *